US011903673B1

(12) United States Patent
Peng (10) Patent No.: US 11,903,673 B1
(45) Date of Patent: Feb. 20, 2024

(54) SYSTEMS AND METHODS OF A HEAD MOUNTED CAMERA WITH FIBER BUNDLE FOR OPTICAL STIMULATION

(71) Applicant: PhotonEdge Inc., Pleasanton, CA (US)

(72) Inventor: Song Peng, Pleasanton, CA (US)

( * ) Notice: Subject to any disclaimer, the term of this patent is extended or adjusted under 35 U.S.C. 154(b) by 633 days.

(21) Appl. No.: 16/233,993

(22) Filed: Dec. 27, 2018

Related U.S. Application Data (60) Provisional application No. 62/612,413, filed on Dec. 30, 2017.

(51) Int. Cl.
| | |
|---|---|
| *A61B 5/00* | (2006.01) |
| *A61B 1/313* | (2006.01) |
| *A61B 1/00* | (2006.01) |
| *A61B 1/04* | (2006.01) |
| *A61N 5/06* | (2006.01) |
| *A61B 90/00* | (2016.01) |

(52) U.S. Cl.
CPC ........ *A61B 5/0042* (2013.01); *A61B 1/00165* (2013.01); *A61B 1/042* (2013.01); *A61B 1/313* (2013.01); *A61B 5/0077* (2013.01); *A61N 5/0622* (2013.01); *A61B 2090/067* (2016.02); *A61B 2503/40* (2013.01); *A61N 2005/063* (2013.01); *A61N 2005/0612* (2013.01)

(58) Field of Classification Search
CPC ....... A61B 5/0042; A61B 1/313; A61B 1/042; A61B 5/0077; A61B 2090/067; A61B 1/00163–00165; A61B 1/00172; A61N 5/0622; A61N 2005/0612; A61N 2005/063; A61N 2005/0642; A61N 2005/0647

See application file for complete search history.

(56) References Cited

U.S. PATENT DOCUMENTS

| | | | | |
|---|---|---|---|---|
| 4,643,521 A | * | 2/1987 | Harstead | G02B 6/352 385/26 |
| 4,725,116 A | * | 2/1988 | Spencer | G02B 6/3604 385/26 |
| 5,304,173 A | * | 4/1994 | Kittrell | A61B 1/00096 600/477 |

(Continued)

OTHER PUBLICATIONS

Helmchen [A Miniature Head-Mounted Two-Photon Microscope: High-Resolution Brain Imaging in Freely Moving Animals, Neuron, vol. 31, 903-912, Sep. 27, 2001 ] (Year: 2001).*

(Continued)

*Primary Examiner* — Oommen Jacob
(74) *Attorney, Agent, or Firm* — RADLO & SU; Peter Su (57) ABSTRACT

Embodiments of the present disclosure are directed to optical instruments and methods with a head mounted camera on a subject to provide a compact and lightweight solution to imaging specimen from the brain of a subject thereby providing closer proximity imaging with minimal or negligible effect to the subject's ability to physically move and rotate freely. The head mounted camera includes a light source for illuminating light through a beamsplitter to an image lens implant, which has been surgically inserted in the brain of the subject. The head mounted camera also includes an image sensor for imaging the top surface of the imaging lens implant and for capturing and transmitting images of neurons from deep inside the brain of the subject to the image sensor.

17 Claims, 10 Drawing Sheets

(56) References Cited

U.S. PATENT DOCUMENTS

| | | | | | |
|---|---|---|---|---|---|
| 5,693,043 | A * | 12/1997 | Kittrell | ............... | A61B 1/00096 606/15 |
| 7,515,782 | B2 * | 4/2009 | Zhang | ................... | G02B 6/3604 385/15 |
| 7,613,371 | B2 * | 11/2009 | Ankerhold | ............ | G02B 6/3604 385/25 |
| 7,881,569 | B2 * | 2/2011 | Zhang | ................... | G02B 6/3604 385/26 |
| 8,380,024 | B1 * | 2/2013 | Zhang | ................... | G02B 6/3604 385/26 |
| 8,781,560 | B2 * | 7/2014 | Bambot | ................ | A61B 5/0059 600/473 |
| 8,826,973 | B2 * | 9/2014 | Moxley | ................... | E21B 43/11 166/77.2 |
| 9,046,659 | B2 * | 6/2015 | Doric | ................... | G02B 6/3604 |
| 9,207,405 | B2 * | 12/2015 | Doric | ................... | G02B 6/3628 |
| 9,357,923 | B2 * | 6/2016 | Courtney | ................. | A61B 8/12 |
| 9,791,683 | B2 * | 10/2017 | Doric | ................... | A61B 5/0071 |
| 2002/0045811 | A1 * | 4/2002 | Kittrell | ............... | A61B 1/00096 600/407 |
| 2004/0007675 | A1 * | 1/2004 | Gillispie | ............ | G01N 21/6408 250/458.1 |
| 2010/0076304 | A1 * | 3/2010 | Teramura | ........... | G01B 9/02091 600/425 |
| 2012/0232404 | A1 * | 9/2012 | Bambot | ................... | G01J 3/027 600/476 |
| 2012/0323112 | A1 * | 12/2012 | Jokerst | ................... | A61B 8/481 600/420 |

OTHER PUBLICATIONS

Mekhail ["Advances in Fibre Microendoscopy for Neuronal Imaging", Opt. Data Process. Storage 2016; 2:30-42]. (Year: 2016).*

Szabo ["Spatially Selective Holographic Photoactivation and Functional Fluorescence Imaging in Freely Behaving Mice with a Fiberscope", Neuron 84, 1157-1169, Dec. 17, 2014]. (Year: 2014).*

Resendez [In Vivo Calcium Imaging to Illuminate Neurocircuit Activity Dynamics Underlying Naturalistic Behavior, Neuropsychopharmacology (2015) 40, 238-256] (Year: 2015).*

* cited by examiner

SYSTEMS AND METHODS OF A HEAD MOUNTED CAMERA WITH FIBER BUNDLE FOR OPTICAL STIMULATION

CROSS REFERENCE TO RELATED APPLICATIONS

The present application claims priority to and the benefit of U.S. Provisional Application Ser. No. 62/612,413 entitled "Head Mounted Camera with Fiber Bundle for Optical Stimulation," filed on 30 Dec. 2017, the disclosure of which is incorporated herein by reference in its entirety.

The present application is related to a co-pending U.S. Nonprovisional application Ser. No. 16/177,372 entitled "Systems and Methods of Rotation Compensation for Brain Optical Imaging and Stimulation," filed on 31 Oct. 2018, which claims priority to U.S. Provisional Application Ser. No. 62/588,088 entitled "Rotation Compensation for Brain Imaging and Stimulation," filed on 17 Nov. 2017, and a co-pending U.S. Nonprovisional application Ser. No. 16/194,383 entitled "Systems and Methods of Multi-Implant Patterned Brain Imaging and. Stimulation," filed on 18 Nov. 2018, which claims priority to U.S. Provisional Application Ser. No. 62/588,898 entitled "Multi-implant Patterned Stimulation," filed on 20 Nov. 2017, the disclosures of which are incorporated by reference herein in their entireties.

BACKGROUND

Technical Field

The present disclosure relates to fields of neuroimaging (or brain imaging technologies) and stimulation, and more particularly to an optical instrument with a head mounted camera for brain fluorescence imaging.

Background Art

Neuroscience is a science discipline gaining an enormous amount of interests from researchers and scientists to enhance human understanding of physical, psychological and neurological conditions of brains for medical treatment and development of artificial intelligence. Microendoscope optical brain imaging provides a tool for the study and unraveling of mystery of neuroscience of animals. Optical fiber microendoscope is designed to image neural activity of animals as minimally invasive or non-invasive solutions.

One conventional solution provides a microendoscope to observe, research and study a free-moving animal with an imaging fiber typically fixed on the head of an animal. As the animal moves in a geographical area, the imaging fiber of the microendoscope gets twisted as the animal turns and rotates in different directions. The resulting torque from the twisting of the imaging fiber from the animal's head potentially could cause the imaging fiber to break. Even if the imaging fiber does not break, the resulting torque on the fixed imaging fiber on the animal's head may be too burdensome that the animal may be constrained from natural movements and instead turn back to comply with the forces as exerted from the torque on the animal, which in effect unnaturally affecting the animal's natural movements and behavior. Another solution is to mount the camera directly on the head. An obvious limitation of this approach is the weight and size of the head mounted camera.

Accordingly, it is desirable to design an optical instrument with functional capabilities that would allow an animal to move freely while capturing optical images without impacting or constrain the natural motions of the animal.

SUMMARY OF THE INVENTION

Embodiments of the present disclosure are directed to optical instruments and methods with a head mounted camera (also referred to a head mounted device) on a subject to provide a compact and lightweight solution to imaging specimen from the brain of a subject to provide closer proximity imaging with minimal or negligible effect to the subject's ability to move or rotate freely. The head mounted camera includes a light source for illuminating light through a beamsplitter to an image lens implant, which has been surgically inserted in the brain of the subject. The head mounted camera also includes an image sensor for capturing and transmitting images of neurons via the lens implant from deep inside the brain of the subject to the image sensor.

To maintain the practicability of the head mounted camera as fairly compact and lightweight, the head mounted camera is design to couple other optical components or computing components. In a first embodiment, the head mounted camera includes a port for coupling to an imaging fiber bundle, which further couples to a spatial light modulator in an optical instrument for generating patterned optical stimulation. The addition of the port to the head mounted camera reduces the overall bulkiness and weight of the head mounted camera by moving additional functions and components external to the head mounted camera. For example, the generation of the patterned optical stimulation function by a spatial light modulator or a laser scanner can be placed external to the head mounted camera.

In a second embodiment, the head mounted camera is coupled to an electrical cable, which is further coupled to a computer, for imaging the brain of the subject. The electrical cable has a first wire for driving electrical power to a light-emitting diode (LED) in the head mounted camera, and a second wire for transferring one or more images from the head mounted camera.

Other embodiments for incorporating additional functions or components for imaging the brain of the subject, either for inclusion in the optical instrument in the first embodiment or as one or more additional computer functions in the second embodiment, can be practiced without departing from the spirits of the present invention.

Broadly stated, a head mounted apparatus, comprising a light source for illuminating light on a subject; an imaging sensor for capturing one or more images of the subject; first imaging optics, communicatively coupled to the imaging sensor, for imaging the subject to the imaging sensor; a port for coupling to an imaging fiber; and second imaging optics for projecting the imaging fiber on the subject.

The structures and methods of the present disclosure are disclosed in detail in the description below. This summary does not purport to define the disclosure. The disclosure is defined by the claims. These and other embodiments, features, aspects, and advantages of the disclosure will become better understood with regard to the following description, appended claims, and accompanying drawings.

Additional features and advantages of embodiments will be set forth in the description, which follows, and in part will be apparent from the description. The objectives and other advantages of the invention will be realized and attained by the structure particularly pointed out in the example embodiments in the written description and claims hereof as well as the appended drawings. It is to be understood that both the foregoing general description and the following detailed description are illustrative and explanatory and are intended to provide further explanation of the invention as claimed.

BRIEF DESCRIPTION OF THE DRAWINGS

The novel features and characteristic of the disclosure are set forth in the appended claims. The disclosure itself, however, as well as a preferred mode of use, further objectives and advantages thereof, will best be understood by reference to the following detailed description of an illustrative embodiment when read in conjunction with the accompanying drawings. One or more embodiments are now described, by way of example only, with reference to the accompanying drawings wherein like reference numerals represent like elements and in which:

DETAILED DESCRIPTION

A description of structural embodiments and methods of the present invention is provided with reference to FIGS. 1-10. It is to be understood that there is no intention to limit the invention to the specifically disclosed embodiments but that the invention may be operated using other features, elements, methods, and embodiments that are known to those of skill in the art. Like elements in various embodiments are commonly referred to with like reference numerals.

Different arrangements described herein are provided by way of example only, and other arrangements and elements can be added or used instead and some elements may be omitted altogether. Also, those skilled in the art will appreciate that many of the elements described herein are functional entities that may be implemented as discrete components or in conjunction with other components, in any suitable combination and location, and various functions could be carried out by software, firmware and/or hardware.

Figure 1:
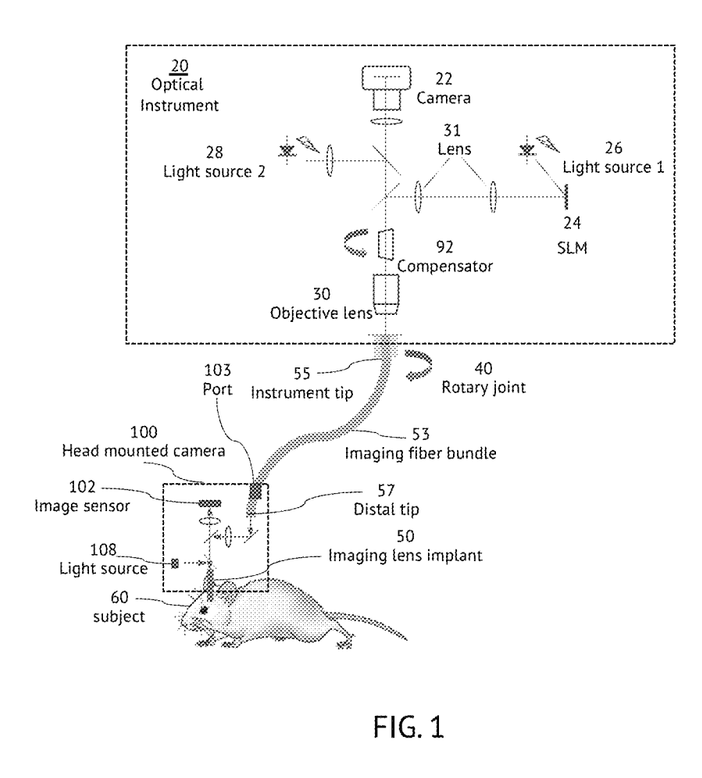
FIG. 1 is a system diagram illustrating one embodiment of an optical instrument coupled to a fiber imaging bundle and a head mounted camera for optical stimulation in accordance with the present invention.

FIG. 1 is a system diagram illustrating one embodiment of an optical instrument 20 coupled to a fiber imaging bundle 53 (or an imaging fiber 52 in FIGS. 4-9) and a head mounted camera 100 with an imaging lens implant into a subject 60 for optical stimulation and imaging. The optical instrument 20 in this embodiment includes a camera 22, a spatial light modulator (SLM) 24 or a laser scanner, a first light source 26, a second light source 28, an objective lens 30, and a rotary joint 40. The optical instrument 20, the imaging fiber bundle 52, and the head mounted camera 100 collectively operate to image samples or specimen of the subject 60 with the following exemplary occurrences. The spatial light modulator 24 generates stimulation pattern, which the object lens 30 and lens 31 image the stimulation pattern onto to an instrument tip 55 of the imaging fiber bundle 53. The imaging fiber bundle 53 transmits the image from the instrument tip 55 to a distal tip 57 of the imaging fiber bundle 53. The imaging lens implant 50 (a GRIN lens or a short piece of imaging fiber) images from the distal tip 57 of the imaging fiber bundle 53 to a top surface of the GRIN lens 50 onto the sample surface and inside the brain of the subject 60. With these process steps, the optical instrument 24 is projecting the stimulation pattern from the spatial light modulator 24 all the way to inside the brain of the subject 60.

Figure 3:
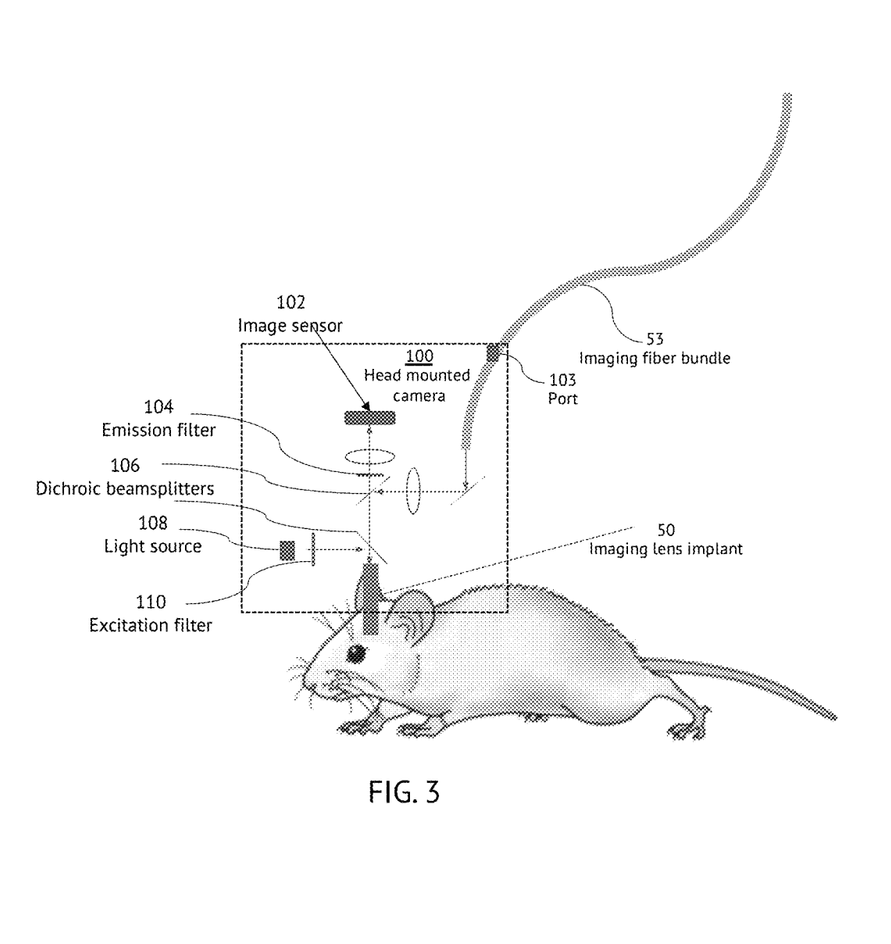
FIG. 3 is a block diagram illustrating the components in the head mounted camera in accordance with the present invention.

The head mounted camera 100, as illustrated in FIG. 1 and further elaborated in FIG. 3, serves as a miniature device close in proximity to the subject to facilitate superior imaging of the brain activities of the subject 60, while allowing the subject to rotate and move freely with little or no friction. The design of the head mounted camera 100 is fairly compact and lightweight, which preferably does not significantly affect the behavior of subject 60. The head mounted camera 100 operates as an intermediate component coupling between the imaging fiber bundle 53 (which the spatial light modulator projects optical patterned stimulation onto the imaging fiber bundle 53) and the imaging lens implant 50 inside the subject 60. The imaging lens implant 50 is surgically inserted into the brain of the subject 60 and serves to relay one or more images from inside the brain of the subject 60 to the head mounted camera 100.

The head mounted camera 100 includes an imaging sensor (also referred to as a camera sensor) 102, an emission filter 104 for fluorescence imaging, dichroic beamsplitters 106, a light source (such as a light emitting diode, LED) 108, an excitation filter 110, and a port 103. In one embodiment, the imaging path of the head mounted camera 100 occurs in the following sequence. The subject 60 possesses samples or specimen inside the brain of the subject 60. The LED 108 illuminates light through the beamsplitter 106 onto the image lens implant 50. The imaging lens implant (or GRIN lens) images one or more samples from the top surface of the GRIN lens to transmit one or more images of neurons deep inside the brain of the subject 60 to outside the brain of the subject 60. The image sensor 102 images the top surface of the GRIN lens 60 and capture the images onto the image sensor 102. The excitation filter 110 can be implemented as a high quality optical-glass filter for selection of the excitation wavelength of light from the light source 108. The dichroic beamsplitters 106 are disposed between the excitation filter 110 and the emission filter 104 for transmitting the emission signal towards a detector. The emission filter 104 is placed in an imaging path for filtering out the excitation range of fluorescence imaging, while transmitting the emission range of fluorescence imaging.

In one embodiment, the head mounted camera 100 includes the port 103 as a distinctive design of the present invention for coupling to the imaging fiber bundle 53 to introduce patterned optical stimulation. The addition of the port 103 alleviates the burden to incorporate more functions and components within the head mounted camera 100 by moving these functions and components external to the head mounted camera 100, which allows the head mounted camera 100 to maintain the fairly compact in size and relatively lightweight without interfering or affecting the free movements of the subject 60. As an example, the generation of the patterned optical stimulation function by a spatial light modulator or a laser scanner can be allocated external to the head mounted camera 100. In the current technology, either the spatial light modulator or the laser scanner may be too bulky, too heavy for placement inside the head mounted camera 100 and for mounting on the head of the subject 60.

In one embodiment, the optical instrument 20 acts as a base station that sits on a platform, such as a table. The optical instrument 20 generates optical stimulation patterns for transmission to the brain subject 60 through the flexible imaging fiber bundle 53. The weight of the head mounted camera 100 on the brain of the subject 60 is minimal or negligible, as to have no effect or little effect to the free rotations and movements of the subject 60.

One of skilled in the art would recognize that additional functionalities and/or components can be added to the optical instrument 20 without departing from the spirits of the present invention. For example, additional functionalities and components that can be added to the optical instrument 20 include, but not limited to, multi-photon imaging/stimulation, holographic imaging/stimulation, and confocal imaging/stimulation.

Figure 2:
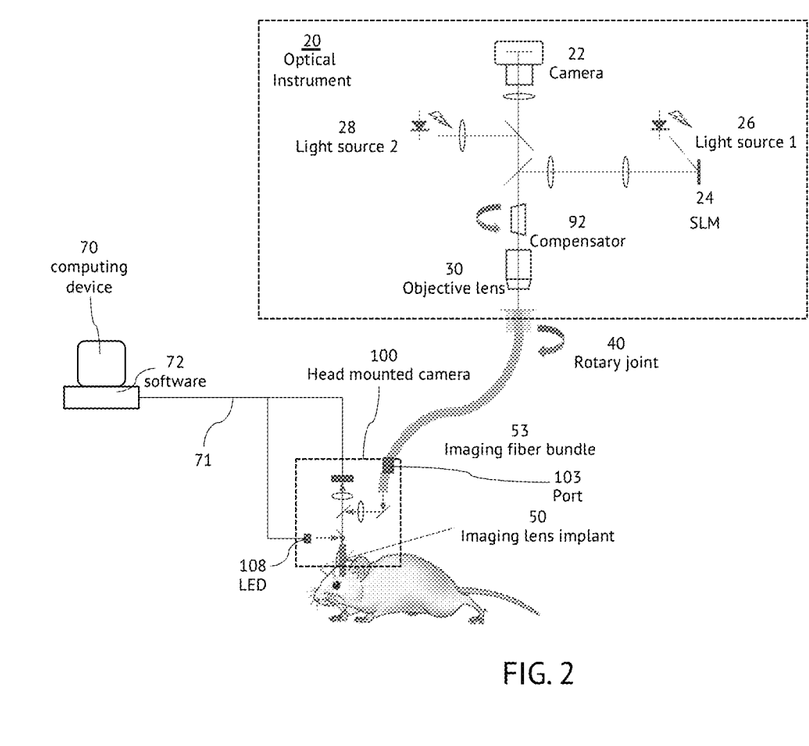
FIG. 2 is a system diagram illustrating another embodiment of a head mounted camera coupled to an electrical cable and a computer for optical imaging in accordance with the present invention.

FIG. 2 is a system diagram illustrating another embodiment of the head mounted camera 60, which is mounted to the head of the subject 60, with an electric cable 71 (or a wireless connection) coupled to the computer 70. The electrical cable 71 has a first wire for driving electrical power to the LED 108, and a second wire for transferring one or more images from the head mounted camera. In the embodiment, the port 103 in the head mounted camera 60 is optional to provide greater functionalities from the optical instrument 20.

Figure 4:
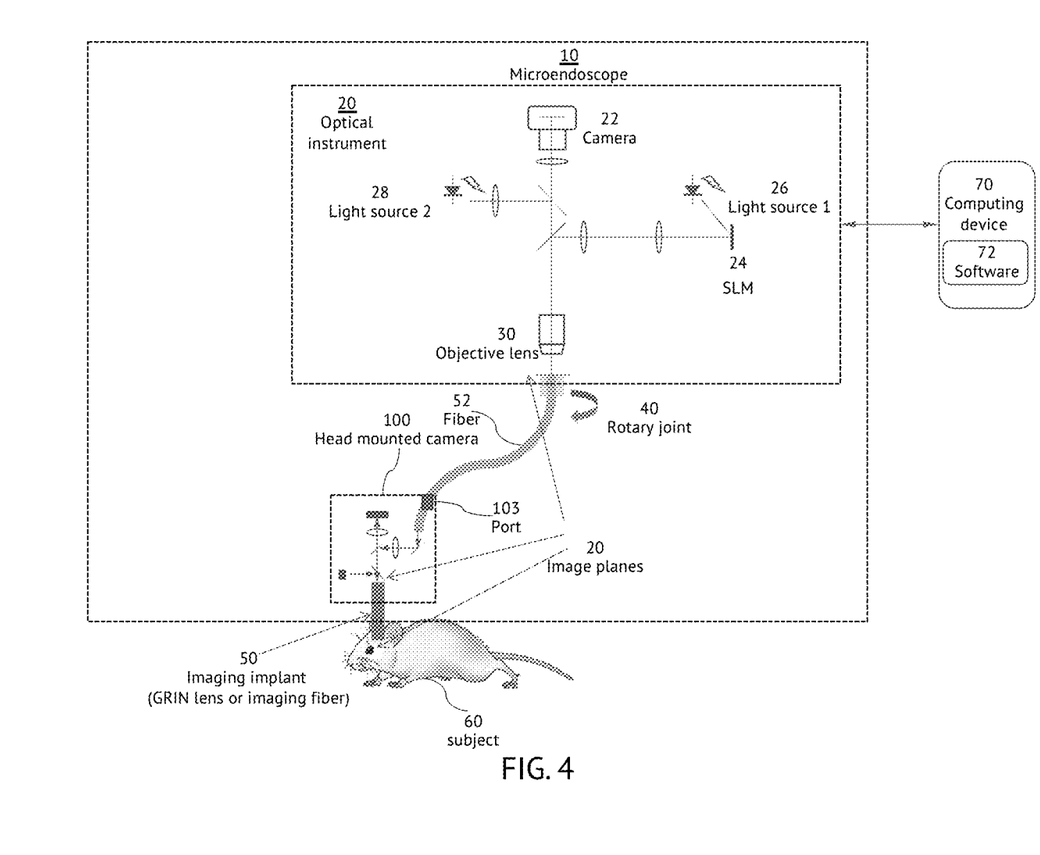
FIG. 4 is a system diagram illustrating a first implementation of microendoscope with a rotary joint for applying the head mounted camera in accordance with the present invention.

FIG. 4 is a system diagram illustrating a first implementation of microendoscope 10 comprising an optical instrument 20, a rotary joint 40, the head mounted camera 100 with the port 103, the imaging implant 50 coupled to a subject 60. The optical instrument 20 includes a camera 22, a spatial light modulator (SLM) 24, a first light source 26, a second light source 28, and an objective lens 30. The rotary joint 40 is disposed between the optical instrument 20 and the imaging implant 50. The rotary joint 40 allows the subject 60 to be able to move freely because a fiber 52 and the imaging implant 50 rotate along the direction and movements of the subject 60. The rotary joint 40, for example, has ball bearings with low-friction, which enables the rotary joint 40 to rotate freely with the subject 60, without affecting the subject's 60 behavior or the rotational direction of the subject 60.

The camera 22 detects and analyzes certain fixed feature of the images or specimen from the subject generated from the tip of the imaging fiber 52. Images inside the camera 22 are also rotating as the rotary joint 40 and the fiber implant 50 move with the subject 60. A computing device 70 is coupled to the optical instrument 20 to extract rotation angles from the position of fixed feature or an image of the specimen of the subject 60 from the camera 22. The computing device 70 includes an imaging software 72 for adjusting and realigning each affected image based with the rotation angles. With the computation on the rotation angles, the spatial light modulator 24 in the microendoscope 10 is able to rotate the stimulation patterns by the specified rotation angles to offset the rotational directions and movements of the subject 60. The microendoscope 10 in the first implementation comprises a system solution without the need of a rotation compensator by a combination of the rotary joint 40 that follows the natural movements of the imaging implant 50 attached to the subject 60, which then the camera 10 receives rotated images from the tip of the imaging implant 50 that the imaging software 72 calculates the amount of rotated angles, followed by the spatial light modulator 24 correspondingly adjusting the projected stimulation pattern by the specified rotated angled on to the brain of the subject 60.

As an example, initially, the spatial light modulator 24 projects a stimulation pattern onto the brain of the subject 60. The imaging implant 50 projects the light pattern to different spots on the brain of the subject 60 depending on the movement of the subject 60. In this example, the imaging implant 50 obtained three neuron cells from the brain of the subject 60. The camera 22 captures the images of three neuron cells in which the images reflect the one or more movements by the subject 60. The imaging software 72 computes to determine that the images have been rotated by 30 degrees from the movements of the subject 60, and therefore the imaging software 72 corrects the images by rotating 30 degrees to reflect the correct orientations of the images. The imaging software 72 also rotates the stimulation patterns on the spatial light modulator 24 by 30 degrees so that the stimulation patterns are projected to the same positions on subject 60.

The imaging implant 50 can be implemented, for example, with a gradient index (GRIN) lens or a short piece of imaging fiber. Alternatively, the rotary joint 40 can also be placed between a gradient index (GRIN) lens implant and the imaging fiber. The subject in instance is an animal, such as a mouse.

The imaging fiber 52 in this implementation is shown with a single imaging fiber, though a bundle of multiple imaging fibers can be implemented with the present invention. For a bundle of multiple imaging fibers, the common ends of the bundle would be coupled to the rotary joint 40, while the distal ends are used to image and stimulate different regions of the subject 60.

Figure 5:
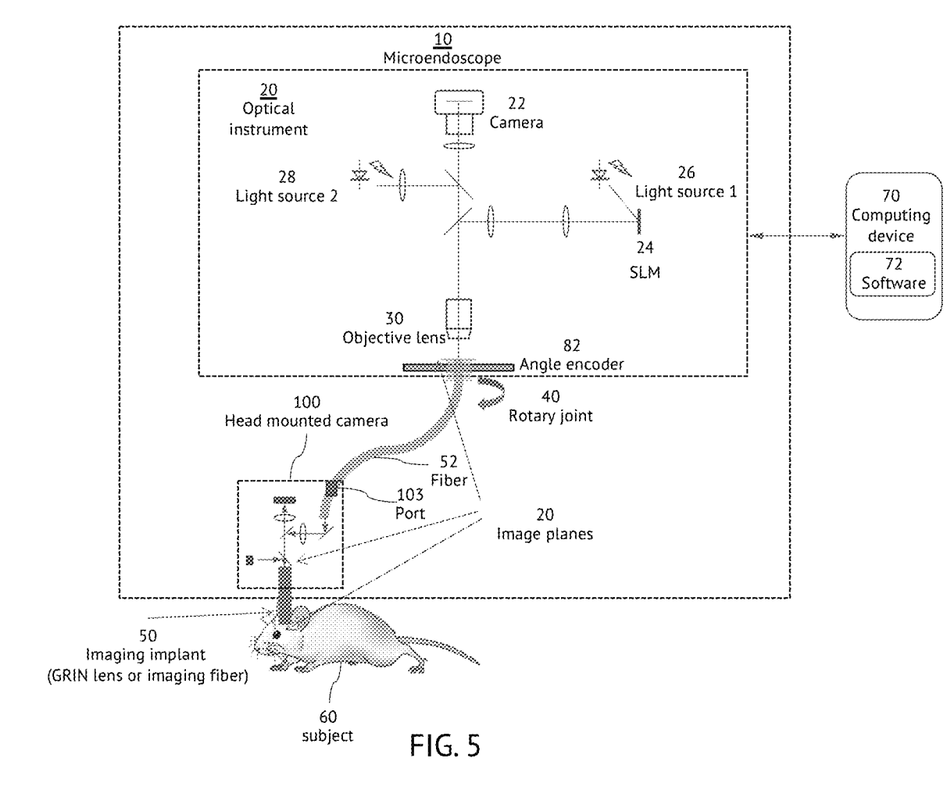
FIG. 5 is a system diagram illustrating a second implementation of microendoscope with a rotary joint and an angle encoder for applying the head mounted camera in accordance with the present invention.

FIG. 5 is a system diagram illustrating a second implementation of microendoscope 10 with a rotary joint 40 and an angle encoder 82 (also referred to as a rotation encoder) with the head mounted camera 100 that includes the port 103. The microendoscope 10 includes the angle encoder 82, which is coupled to the rotary joint 40, for a more accurate read out of the rotation angles with a shorter delay. The angle encoder 82 produces angular information of the images captured by the imaging plant 50 to the computing device 70 for realigning the images, as well as for the spatial light modulator 24 to rotate the stimulation patterns.

Figure 6:
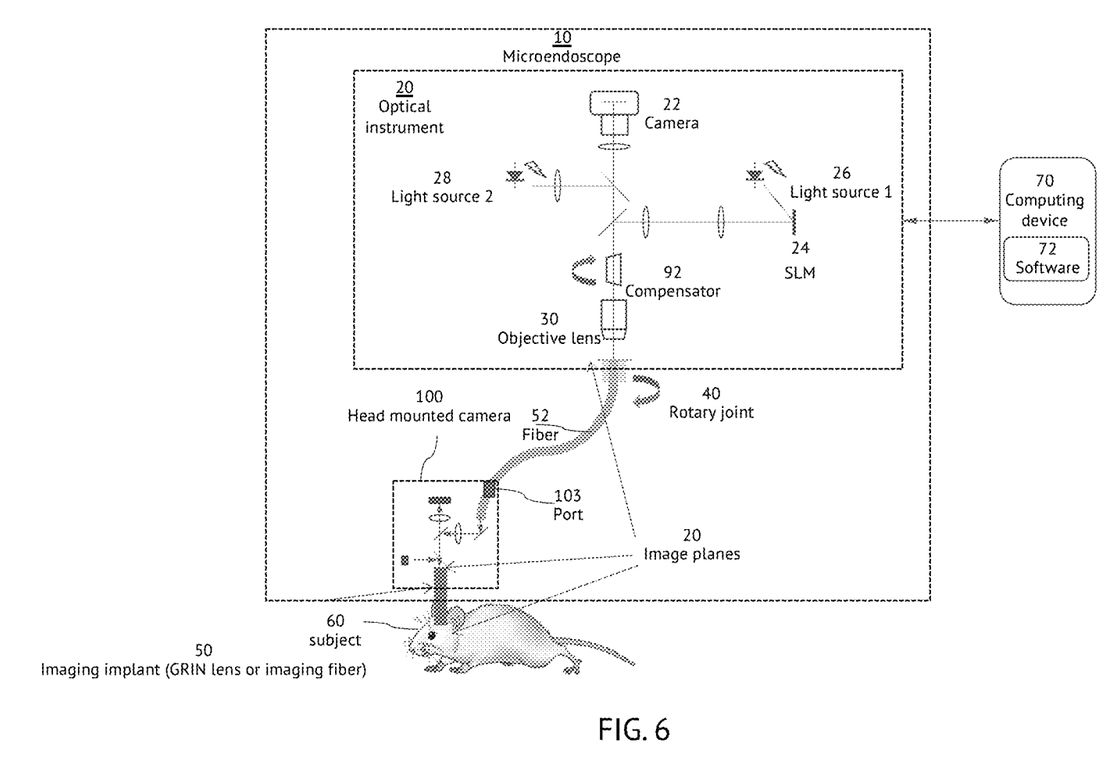
FIG. 6 is a system diagram illustrating a third implementation of microendoscope with a rotary joint and a rotation compensator for applying the head mounted camera in accordance with the present invention.

FIG. 6 is a system diagram illustrating a third implementation of the microendoscope 10 with the rotary joint 40, a rotation compensator 92 and the head mounted camera 100 that includes the port 103. The rotation compensator 92 serves to rotate back an optical image received from the imaging implant 50 of the subject 60. One suitable implementation of the rotation compensator 92 is a Dove prism. The correlation between an optical image and the Dove prism is that the output image rotates at twice the rotation speed of the Dove prism. One way to achieve this rotation ratio employs mechanical mechanisms to link the rotary joint 40 and the rotation compensator 92 which yield the rotation compensator 92 rotates at the half the speed relative to the rotational speed of the rotary joint 40. Preferably, in the example of implementing with a Dove prism, the rotation compensator 92 would rotate in the same direction as the direction of the rotary joint 40. The output image from the rotation compensator 92 remains stationary even as the subject 60 moves around. The stimulation patter from the spatial light modulator 24 also stays stationary on the specimen.

Optionally, an electrical motor can be added to enhance power assistance to the rotation compensator 92, particularly in implementations where a chosen prism may be on the heavy side, as to hinder the movements of the subject. The addition of the electrical motor would reduce resistance that would weigh on the subject 60.

Figure 7:
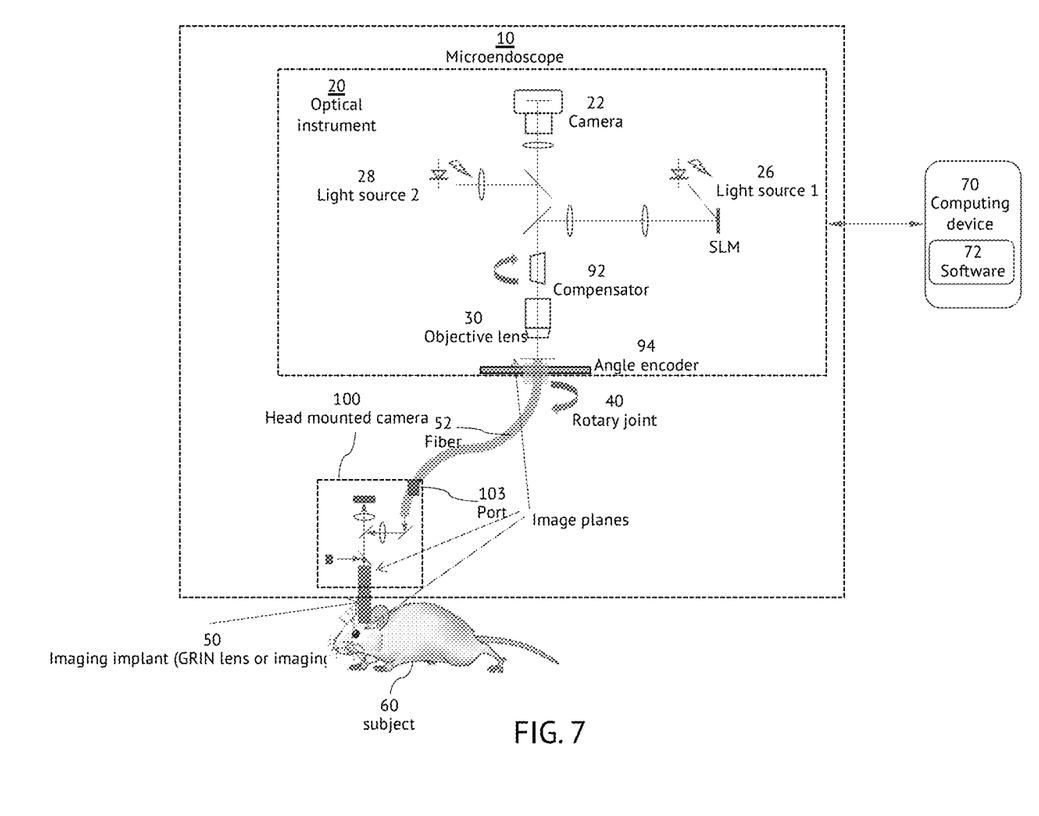
FIG. 7 is a system diagram illustrating a fourth implementation of microendoscope with a rotary joint, a rotation compensator and an angle encoder for applying the head mounted camera in accordance with the present invention.

FIG. 7 is a system diagram illustrating a fourth implementation of the microendoscope 10 with the rotary joint 40, the rotation compensator 92, an angle encoder 94, and the head mounted camera 100 that includes the port 103. The combination of the encoder 94 and the rotary joint 40 is able to directly feed a rotation angle to a motor to rotate the rotation compensator, thereby eliminates any mechanical connection between the rotary joint and the rotation compensator. Alternatively, without a rotation encoder, other implementations described above to obtain a rotated angle from an optical image can be used to control the rotation compensator for compensating the orientation of the rotated optical image.

Figure 8:
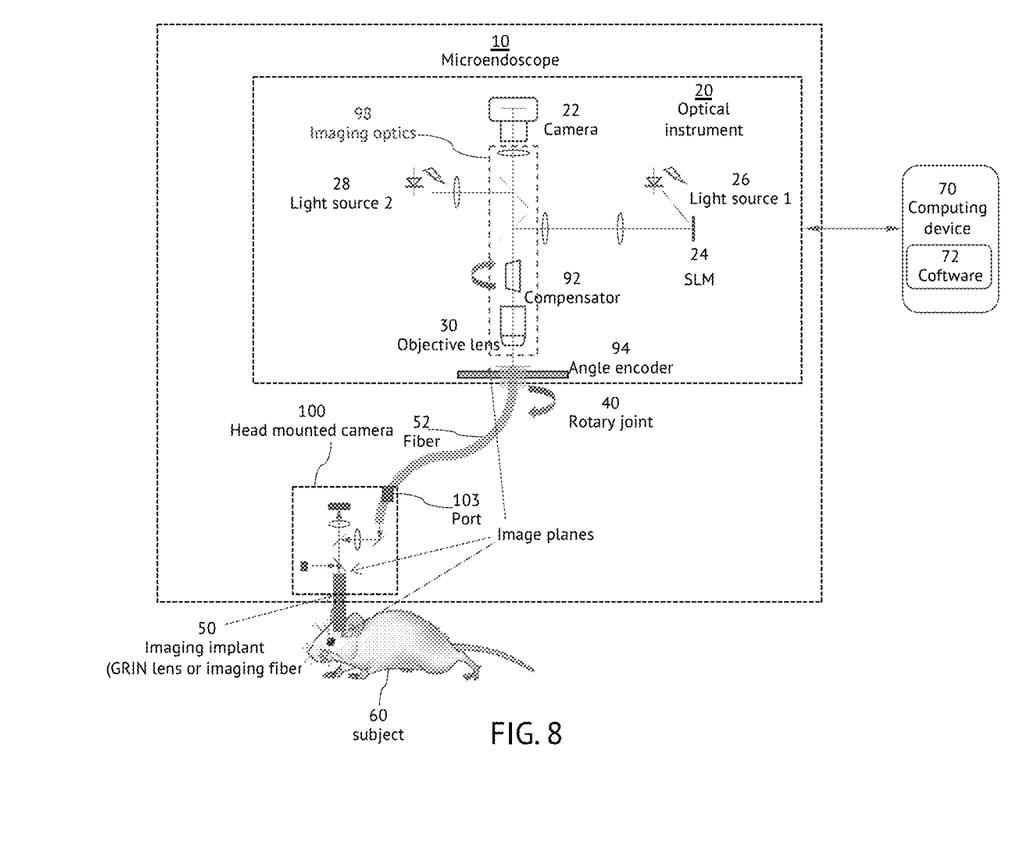
FIG. 8 is a system diagram illustrating the fourth implementation of microendoscope with imaging optics, the rotary joint and the angle encoder for applying the head mounted camera in accordance with the present invention.
Figure 9:
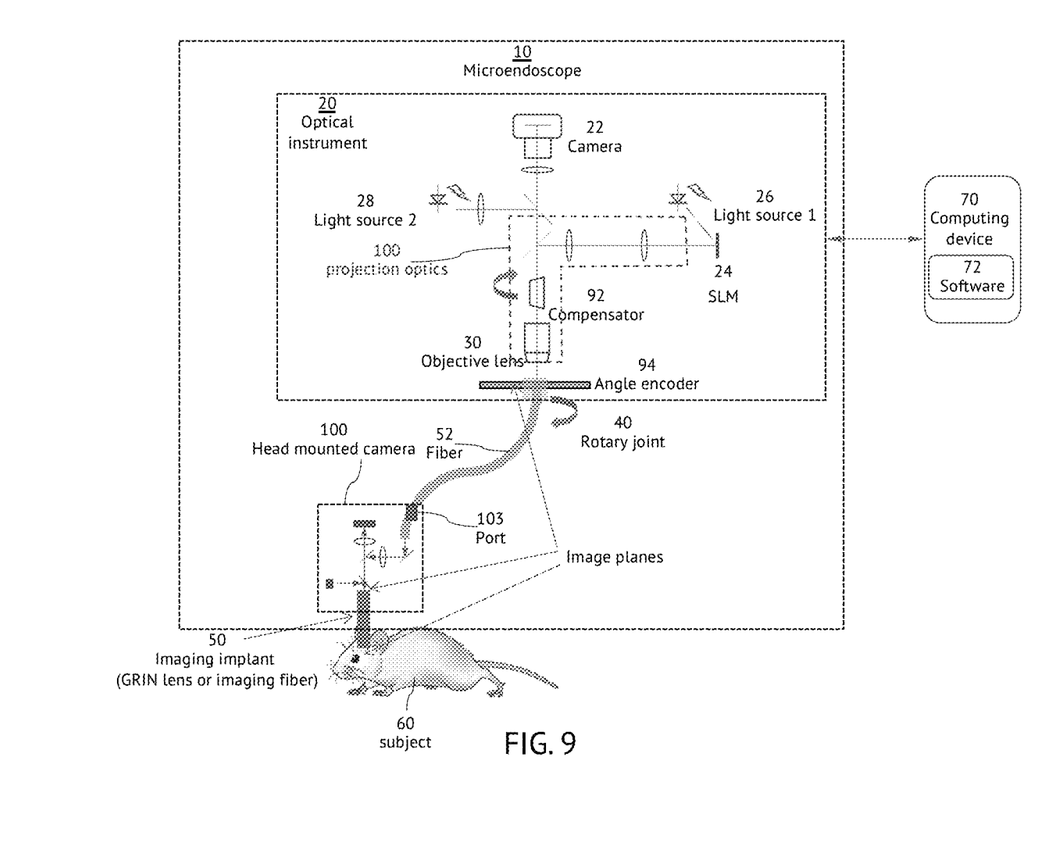
FIG. 9 is a system diagram illustrating the fourth implementation of microendoscope with projection optics, the rotary joint and the angle encoder for applying the head mounted camera in accordance with the present invention.

In one alternative, FIG. 8 is a system diagram illustrating the fourth implementation of microendoscope with imaging optics 98, the rotary joint, the angle encoder 94, and the head mounted camera 100 that includes the port 103. The light source 28 provides illumination for the imaging optics 98. The imaging optics 98 shows one example of the imaging path from the camera 22. In this implementation, the imaging optics 98 represent several optical components, including the objective lens, the rotation compensator 92 and optical lens. In another alternative, FIG. 9 is a system diagram illustrating the fourth implementation of microendoscope with projection optics 100, the rotary joint 40, the angle encoder 94, and the head mounted camera 100 that includes the port 103. The projection optics 100 illustrates one example of the light path projected from the spatial light modulator 24. The projection optics 100 in this implementation includes the objective lens 30, the rotation compensator 92, and other optical components.

Another implementation provides a video camera system for monitoring and detecting the movements of an animal, which the data monitored or detected are fed back to correspondingly adjust the rotating platform of a microendoscope. One advantage of the video camera solution is that the optical system of the microendoscope would typically require no further modifications to track the brain imaging of an animal.

Figure 10:
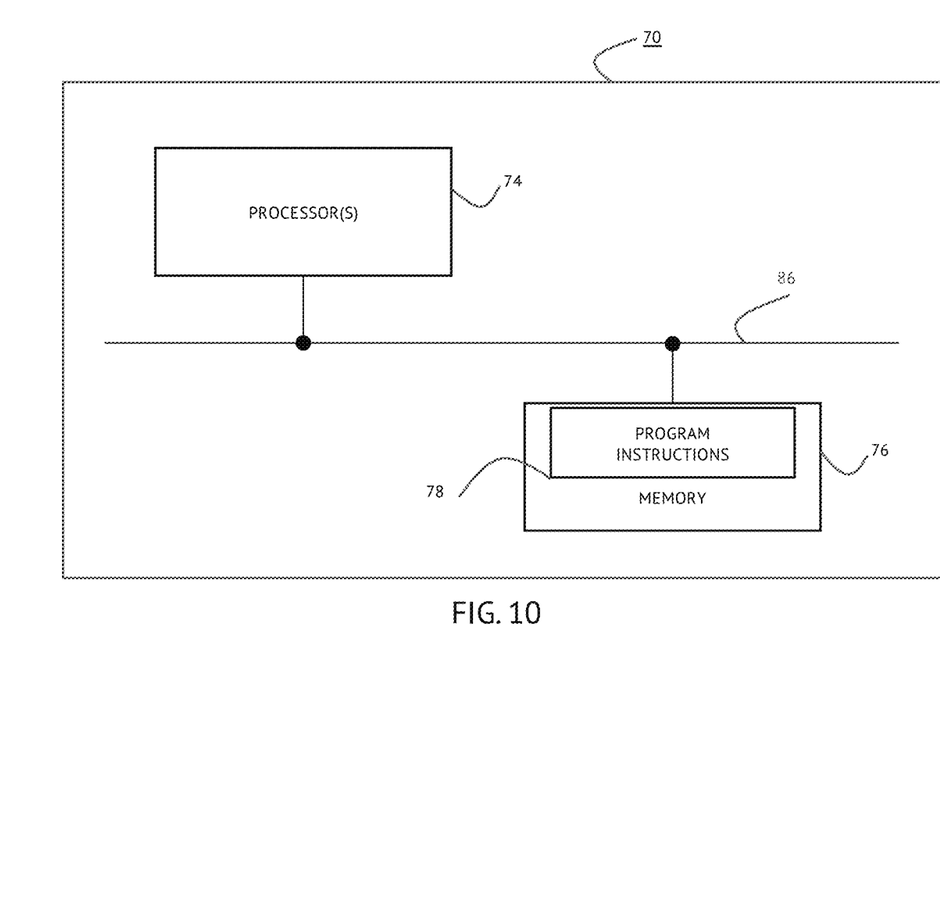
FIG. 10 is a simplified diagram of a computer processing system in accordance with the present invention.

Various functions described herein, such as in FIGS. 1-9 above, could be carried out by a processing system 70, as shown in FIG. 10. The system 70 includes at least one processor 74 and memory 76, coupled together via a bus 86. The processing system 70 may be, for example, incorporated in a separate controller controlling the element(s) of the microendoscope 10 (e.g., the spatial light modulator 24) or its components may be distributed fully or partially across the element(s) of the microendoscope 10. Various examples are possible.

In one embodiment, the processor(s) 74 may be dedicated processor(s) or general purpose processor(s) configured to execute computer-readable program code. The memory 76 may be volatile or non-volatile non-transitory computer-readable medium or media, now known or later developed. The memory 76 may hold program logic comprising program instructions 78 (e.g., machine language instructions) executable by the processor(s) 74 to carry out various functions described herein. Additionally, the memory 76 may store any other data, such as data used by the processor(s) 74 in the execution of the program instructions 78. However, any additional data may also be held in other data storage location(s) separate from the memory 76.

Further, although not shown in FIG. 7, the processing system 70 may include a number of interfaces, such as user interface(s), communication interface(s) (e.g., an interface for communicating data to/from the memory 76, etc.), and/or the like. Also, other elements (e.g., modules, input lines, buses, etc.) may be included as well.

As used herein, any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. It should be understood that these terms are not intended as synonyms for each other. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B are satisfied by any one of the following: A is true (or present) and B is false (or not present), A is false (or not present) and B is true (or present), and both A and B are true (or present).

The terms "a" or "an," as used herein, are defined as one or more than one. The term "plurality," as used herein, is defined as two or more than two. The term "another," as used herein, is defined as at least a second or more.

The invention can be implemented in numerous ways, including as a process, an apparatus, and a system. In this specification, these implementations, or any other form that the invention may take, may be referred to as techniques. In general, the order of the connections of disclosed apparatus may be altered within the scope of the invention.

The present invention has been described in particular detail with respect to some possible embodiments. Those skilled in the art will appreciate that the invention may be practiced in other embodiments. First, the particular naming of the components, capitalization of terms, the attributes, data structures, or any other programming or structural aspect is not mandatory or significant, and the mechanisms that implement the invention or its features may have different names, formats, or protocols. Further, the system may be implemented via a combination of hardware and software, as described, or entirely in hardware elements. Also, the particular division of functionality between the various system components described herein is merely exemplary, and not mandatory; functions performed by a single system component may instead be performed by multiple components, and functions performed by multiple components may instead be performed by a single component. An ordinary artisan should require no additional explanation in developing the methods and systems described herein but may nevertheless find some possibly helpful guidance in the preparation of these methods and systems by examining standard reference works in the relevant art.

These and other changes can be made to the invention in light of the above detailed description. In general, in the following claims, the terms used should not be construed to limit the invention to the specific embodiments disclosed in the specification and the claims, but should be construed to include all methods and systems that operate under the claims set forth herein below. Accordingly, the invention is not limited by the invention, but instead its scope is to be determined entirely by the following claims.

What is claimed and desired to be secured by Letters Patent of the United States is:

1. A head mounted apparatus, comprising:
    a light source for illuminating light on a subject;
    an imaging sensor for capturing one or more images of the subject;
    first imaging optics, communicatively coupled to the imaging sensor, for forming a first image of the subject to the imaging sensor;
    a port for coupling to an imaging fiber, the imaging fiber including a plurality of cores, the imaging fiber having a distal tip and an instrument end; and
    second imaging optics for forming a second image of the end at the distal tip of the imaging fiber on the subject;
    wherein the light source, the imaging sensor, the first imaging optics, the port and the second imaging optics are part of the head mounted apparatus,
    wherein the imaging fiber having the distal tip coupled to the port and the instrument end coupled externally to an optical instrument;
    wherein the optical instrument comprises a rotation compensator disposed in an optical path for compensating the image rotation caused by the movement of the subject.

2. The apparatus of claim 1, wherein the optical instrument comprises a spatial light modulator (SLM) to provide patterned stimulation to the subject.

3. The apparatus of claim 1, further comprising a rotary joint coupled between the imaging fiber and the optical instrument, the rotary joint allowing the imaging fiber to rotate freely with respect to the optical instrument.

4. The apparatus of claim 1, wherein the optical instrument comprises the imaging sensor for capturing images of the subject.

5. The apparatus of claim 1, wherein the optical instrument comprises one or more imaging optics for imaging the instrument end of the fiber onto a camera.

6. The apparatus of claim 1, wherein the optical instrument comprises one or more projection optics for imaging the SLM onto the instrument end of the fiber.

7. The apparatus of claim 1, wherein the optical instrument comprises the light source for illuminating the subject.

8. The apparatus of claim 1, wherein the optical instrument comprises the light source for stimulating the subject.

9. The apparatus of claim 1, further comprising an imaging implant for insertion into the subject to image one or more tissues inside the subject, and projecting one or more images external to the subject.

10. The apparatus of claim 9, wherein the imaging implant comprises a gradient index (GRIN) lens.

11. The apparatus of claim 9, wherein the imaging implant comprises an imaging fiber.

12. The apparatus of claim 1, wherein the optical instrument comprises an angle encoder, coupled to a rotary joint, for reading out the rotating angle of the instrument end of the imaging fiber as the subject moves.

13. The apparatus of claim 3, wherein the rotation compensator comprises a Dove prism, the Dove prism rotating at half of the speed of the rotary.

14. The apparatus of claim 1, wherein the instrument comprises:
    an angle encoder, coupled to the rotary joint, for reading out the rotating angle of the instrument end of the imaging fiber as the subject moves;
    the rotation compensator driven by a motor; and
    a controller for reading the angle information from the angle encoder and controlling the rotation compensation based on the received angle information.

15. The apparatus of claim 1, wherein the optical instrument comprises a multi-photon imaging and stimulation device for imaging and stimulating the subject via the imaging fiber.

16. The apparatus of claim 1, wherein the optical instrument comprises a holographic imaging and stimulation device for imaging and stimulating the subject via the imaging fiber.

17. The apparatus of claim 1, wherein the optical instrument comprises a laser confocal imaging and stimulation device for imaging and stimulating the subject via the imaging fiber.

* * * * *